(12) United States Patent
Fujiwara et al.

(10) Patent No.: US 8,563,309 B2
(45) Date of Patent: Oct. 22, 2013

(54) PRIMITIVE ORGAN-LIKE STRUCTURE COMPRISING KERATINOCYTES AND HAIR PAPILLA CELLS

(75) Inventors: Shigeyoshi Fujiwara, Yokohama (JP); Jiro Kishimoto, Yokohama (JP); Tsutomu Soma, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 765 days.

(21) Appl. No.: 12/306,649

(22) PCT Filed: Jun. 27, 2007

(86) PCT No.: PCT/JP2007/063333
§ 371 (c)(1),
(2), (4) Date: Dec. 24, 2008

(87) PCT Pub. No.: WO2008/001938
PCT Pub. Date: Jan. 3, 2008

(65) Prior Publication Data
US 2009/0280469 A1    Nov. 12, 2009

(30) Foreign Application Priority Data
Jun. 27, 2006   (JP) ................................ 2006-176763

(51) Int. Cl.
*C12N 15/02*   (2006.01)

(52) U.S. Cl.
USPC ......................................... 435/375; 435/384

(58) Field of Classification Search
None
See application file for complete search history.

(56) References Cited

U.S. PATENT DOCUMENTS

2002/0114772 A1   8/2002   Morgan et al.

OTHER PUBLICATIONS

Lin et al. Induction of Ureter Branching as a Response to Wnt-2b Signaling During Early Kidney Organogenesis Develop. Dyn., 2001, vol. 222, pp. 26-39.*
Meijer et al. GSK-3-Selective Inhibitors Derived from Tyrian Purple Indirubins Chemistry & Biology, 2003, vol. 10, pp. 1255-1266.*
Nanba et al. Role of Shh in hair follicle morphogenesis. Develop. Growth Differ., 2003, vol. 45, pp. 231-239.*
Supplementary European Search Report dated Oct. 23, 2009 in corresponding EP 07768103.9, 8 pages.
Banerjee et al., "Application of hanging drop technique for stem cell differentiation and cytotoxicity studies," Cytotechnology, 2006, 51:1-5.
Havlickova et al., "Towards optimization of an organotypic assay system that imitates human hair follicle-like epithelial-mesencymal interactions," Brutish Journal of Dermatology, 2004, 151:753-765.
Kobayashi et al., "Wnt4-transformed mouse embryonic stem cells differentiate into renal tubular cells," Biochemical and Biophysical Research Communications, 2005, 336:585-595.
Krugluger et al., "Reorganization of hair follicles in human skin organ culture induced by cultured human follicle-derived cells," Experimental Dermatology, 2005, 14:580-585.
Soma et al., "Generation and characterization of three-dimensional human hair follicle model using hanging drop culture system," Journal of Investigative Dermatology, Apr. 2008, 128(1):S150.
Watt et al., "Epidermal stem cells: an update," Current Opinion in Genetics & Development, 2006, 16:518-524.
Bull et al., "Contrasting Localization of c-Myc with Other Myc Superfamily Transcription Factors in the Human Hair Follicle and During the Hair Growth Cycle," J. Invest. Dermatol., Apr. 2001, 116(4):617-622.
Kishimoto et al., "Selective activation of the versican promoter by epithelial-mesenchymal interactions during hair follicle development," Proc. Natl. Acad. Sci. USA, Jun. 1999, 96:7336-7341.
Kishimoto et al., "Wnt signaling maintains hair inducing activity," Exp. Med., 2000, 18(13):1817-1820.
Kishimoto et al., "Wnt signaling maintains the hair-inducing activity of the dermal papilla," Gene Dev., 2000, 14:1181-1185.
Lichti et al., "In Vivo Regulation of Murine Hair Growth: Insights from Grafting Defined Cell Populations onto Nude Mice," J. Invest. Dermatol., Jul. 1993, 101(1,Supp):124S-129S.
Sato, Noboru, "Activation of Wnt signaling maintains self-renewal of human and mouse embryonic stem cells," Experimental Medicine, 2004, 22(7):962-965.
Soma et al., "Recent progress of hair biology and regeneration of human hair follicle," Organ Biology, 2005, 12(4):311-322.
Weger et al., "Igfbp3 Modulates Cell Proliferation in the Hair Follicle," J. Invest. Dermatol., Oct. 2005, 125(4):847-849.
Kishimoto, Jiro, "Wnt signals retain the Ability of Inducing Hair Follicles," Exp. Med., 2000, 18(13):1817-1820, with partial English translation, 7 pages.
Soma et al., "Recent progress of hair biology and regeneration of human hair follicle," Organ Biology, 2005, 12(4):311-322, with partial English translation, 10 pages.
Report of Zhejiang College of Zhejiang University of Technology (Pharmacology Version), 2004, 33(4):370-374.

* cited by examiner

*Primary Examiner* — Deborah Crouch
(74) *Attorney, Agent, or Firm* — Foley & Lardner LLP

(57) ABSTRACT

The present invention provides a method of producing a cell mass capable of serving as a primitive organ-like structure comprised of a plurality of somatic cell types of somatic origin, comprising: preparing cultures containing the plurality of types of somatic cells; mixing the plurality of types of somatic cell cultures followed by adding a Wnt signal activator to the mixed cell culture; subjecting the culture containing the Wnt signal activator to non-plate contact culturing over a predetermined time period; and replacing the medium of the culture cultured by the non-plate contact culturing with medium not containing Wnt signal activator and further culturing for a predetermined time period; wherein, at least one type of the plurality of somatic cells is maintained in an undifferentiated state.

4 Claims, 10 Drawing Sheets

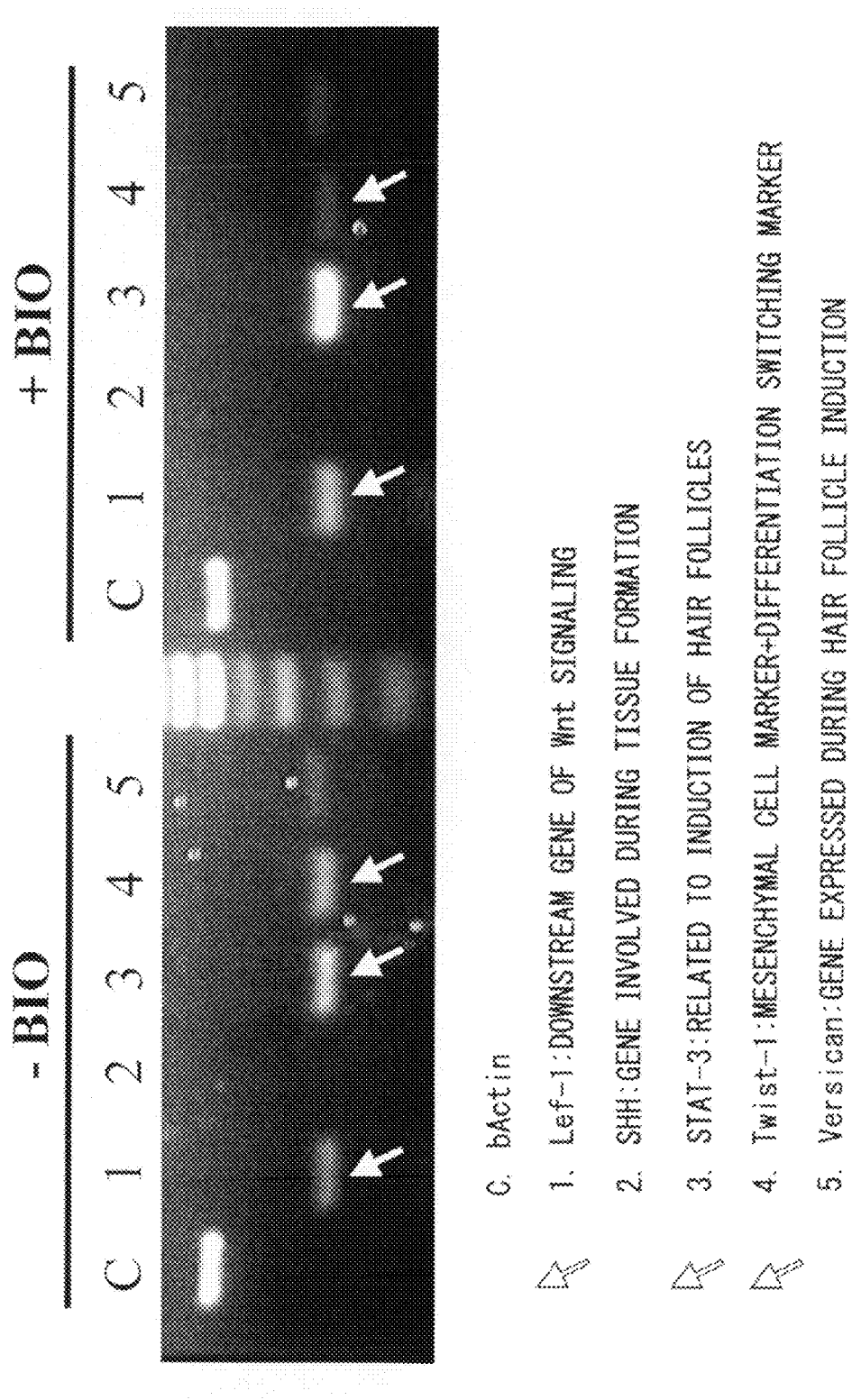

Fig. 8

PRODUCTION OF CELL MASS BY HANGING DROP METHOD BIO (+) 1 week

BIO (−) (START OF DIFFERENTIATION)   0day   3Days

Wnt3a / RT-PCR

Wnt3a IS A RARELY EXPRESSED GENE INVOLVED ORGANOGENESIS AND EPITHELIAL-MESENCHYMAL INTERACTION (EMI)

BIO (+) >MAINTENANCE OF UNDIFFERENTIATED STATE>FORMATION OF CELL MASS

BIO (−) >START OF DIFFERENTIATION>PROMOTION OF INTRACELLULAR EMI-LIKE INTERACTION

_US 8,563,309 B2_

SEQUENCE LISTING

```
<160> NUMBER OF SEQ ID NOS: 22

<210> SEQ ID NO 1
<211> LENGTH: 27
<212> TYPE: DNA
<213> ORGANISM: Artificial
<220> FEATURE:
<223> OTHER INFORMATION: Sense Primer

<400> SEQUENCE: 1
gctatcaacc agattcttgg cagaagg                                    27

<210> SEQ ID NO 2
<211> LENGTH: 27
<212> TYPE: DNA
<213> ORGANISM: Artificial
<220> FEATURE:
<223> OTHER INFORMATION: Antisense Primer

<400> SEQUENCE: 2
cagctgtcat tcttggacct gtacctg                                    27
```

```
<210> SEQ ID NO 3
<211> LENGTH: 27
<212> TYPE: DNA
<213> ORGANISM: Artificial
<220> FEATURE:
<223> OTHER INFORMATION: Sense Primer

<400> SEQUENCE: 3
ctacgagtcc aaggcacata tccactg                                           27

<210> SEQ ID NO 4
<211> LENGTH: 27
<212> TYPE: DNA
<213> ORGANISM: Artificial
<220> FEATURE:
<223> OTHER INFORMATION: Antisense Primer

<400> SEQUENCE: 4
tccaggaaag tgaggaagtc gctgtag                                           27

<210> SEQ ID NO 5
<211> LENGTH: 28
<212> TYPE: DNA
<213> ORGANISM: Artificial
<220> FEATURE:
<223> OTHER INFORMATION: Sense Primer

<400> SEQUENCE: 5
aagaccggcg tccagttcac tactaaag                                          28

<210> SEQ ID NO 6
<211> LENGTH: 28
<212> TYPE: DNA
<213> ORGANISM: Artificial
<220> FEATURE:
<223> OTHER INFORMATION: Antisense Primer

<400> SEQUENCE: 6
ggtcaagtgt ttgaattctg cagagagg                                          28

<210> SEQ ID NO 7
<211> LENGTH: 28
<212> TYPE: DNA
<213> ORGANISM: Artificial
<220> FEATURE:
<223> OTHER INFORMATION: Sense Primer

<400> SEQUENCE: 7
tccaagttat gttggtgcac tttgtgag                                          28

<210> SEQ ID NO 8
<211> LENGTH: 28
<212> TYPE: DNA
<213> ORGANISM: Artificial
<220> FEATURE:
<223> OTHER INFORMATION: Antisense Primer

<400> SEQUENCE: 8
tcaaacatct tgtcattgag gcctatcc                                          28

<210> SEQ ID NO 9
<211> LENGTH: 25
<212> TYPE: DNA
<213> ORGANISM: Artificial
<220> FEATURE:
<223> OTHER INFORMATION: Sense Primer
```

-continued

<400> SEQUENCE: 9
ggccaggtac atcgacttcc tctac                                    25

<210> SEQ ID NO 10
<211> LENGTH: 26
<212> TYPE: DNA
<213> ORGANISM: Artificial
<220> FEATURE:
<223> OTHER INFORMATION: Antisense Primer

<400> SEQUENCE: 10
tctccttctc tggaaacaat gacatc                                   26

<210> SEQ ID NO 11
<211> LENGTH: 24
<212> TYPE: DNA
<213> ORGANISM: Artificial
<220> FEATURE:
<223> OTHER INFORMATION: Sense Primer

<400> SEQUENCE: 11
cgcgagaaga tgacccagat catg                                     24

<210> SEQ ID NO 12
<211> LENGTH: 21
<212> TYPE: DNA
<213> ORGANISM: Artificial
<220> FEATURE:
<223> OTHER INFORMATION: Antisense Primer

<400> SEQUENCE: 12
ccacaggact ccatgcccac g                                        21

<210> SEQ ID NO 13
<211> LENGTH: 22
<212> TYPE: DNA
<213> ORGANISM: Artificial
<220> FEATURE:
<223> OTHER INFORMATION: Sense Primer

<400> SEQUENCE: 13
caggaactac gtggagatca tg                                       22

<210> SEQ ID NO 14
<211> LENGTH: 23
<212> TYPE: DNA
<213> ORGANISM: Artificial
<220> FEATURE:
<223> OTHER INFORMATION: Antisense Primer

<400> SEQUENCE: 14
ccatcccacc aaaactcgat gtc                                      23

<210> SEQ ID NO 15
<211> LENGTH: 27
<212> TYPE: DNA
<213> ORGANISM: Artificial
<220> FEATURE:
<223> OTHER INFORMATION: Sense Primer

<400> SEQUENCE: 15
gaagttctct cgggatttct tggatcc                                  27

<210> SEQ ID NO 16
<211> LENGTH: 25
<212> TYPE: DNA

-continued

<213> ORGANISM: Artificial
<220> FEATURE:
<223> OTHER INFORMATION: Antisense Primer

<400> SEQUENCE: 16
cggttgtggg tatcaatgaa gatgg                                          25

<210> SEQ ID NO 17
<211> LENGTH: 20
<212> TYPE: DNA
<213> ORGANISM: Artificial
<220> FEATURE:
<223> OTHER INFORMATION: Sense Primer

<400> SEQUENCE: 17
gggcacctca tcacacgact                                                20

<210> SEQ ID NO 18
<211> LENGTH: 20
<212> TYPE: DNA
<213> ORGANISM: Artificial
<220> FEATURE:
<223> OTHER INFORMATION: Antisense Primer

<400> SEQUENCE: 18
ggcccaattc ccactccctt                                                20

<210> SEQ ID NO 19
<211> LENGTH: 24
<212> TYPE: DNA
<213> ORGANISM: Artificial
<220> FEATURE:
<223> OTHER INFORMATION: Sense Primer

<400> SEQUENCE: 19
ttctctccgt cctcggattc tctg                                           24

<210> SEQ ID NO 20
<211> LENGTH: 26
<212> TYPE: DNA
<213> ORGANISM: Artificial
<220> FEATURE:
<223> OTHER INFORMATION: Antisense Primer

<400> SEQUENCE: 20
cagcagaagg tgatccagac tctgac                                         26

<210> SEQ ID NO 21
<211> LENGTH: 20
<212> TYPE: DNA
<213> ORGANISM: Artificial
<220> FEATURE:
<223> OTHER INFORMATION: Sense Primer

<400> SEQUENCE: 21
acagccagcg ctacaaagtt                                                20

<210> SEQ ID NO 22
<211> LENGTH: 20
<212> TYPE: DNA
<213> ORGANISM: Artificial
<220> FEATURE:
<223> OTHER INFORMATION: Antisense Primer

<400> SEQUENCE: 22
tagcagtgca cgtcctcctt                                                20

PRIMITIVE ORGAN-LIKE STRUCTURE COMPRISING KERATINOCYTES AND HAIR PAPILLA CELLS

CROSS-REFERENCE TO RELATED APPLICATIONS

This application is a National Stage application of PCT/JP2007/063333, filed Jun. 27, 2007, which claims priority from Japanese application JP 2006-176763, filed Jun. 27, 2006.

TECHNICAL FIELD

The present invention relates to a method for producing a cell mass capable of serving as a primitive organ-like structure comprised of a plurality of cell types of somatic origin, and to a cell mass produced according to that method.

BACKGROUND ART

Due to the remarkable advances made in the field of medicine in recent years, opportunities for saving lives are continuing to increase by eliminating the causes of diseases through, for example, systematic therapeutic techniques in the form of the surgical excision of cancer or living donor transplant techniques for tissues and organs. However, there are cases in which patients suffer a considerable decrease in QOL accompanying excision of an affected area. In addition, there are limitations on treatment dependent upon living donor transplants due to such factors as a shortage of transplant donors and the occurrence of rejection. If it were possible to regenerate a tissue or organ that has been lost due to surgical treatment or an unforeseen accident, then it would be possible to considerably improve the QOL of patients. In addition, regenerative medicine also makes it possible to resolve the problems confronting living donor transplants. From this viewpoint, the degree of expectations being placed on regenerative medicine is high.

Technologies in which regenerative medicine has been successful are primarily related to comparatively simple tissue in terms of morphology or function in the manner of artificial skin, artificial bone and artificial teeth. Reconstructed artificial skin and artificial bone is incorporated into cells enabling the providing of signals required for tissue construction. However, there have been limitations on the repertoire of differentiation of artificial skin and artificial bone by regenerative medicine techniques. For example, although allogenic keratinocytes or skin fibroblasts and the like differentiate into structures in the form of the epidermis, are incorporated by surrounding organs to eventually have a horny layer or basal layer having barrier properties, there has been reported to be no derivation of secondary derivatives such as hair follicles, sebaceous glands or sweat glands.

Body tissue normally contains both cells that are able to self-replicate and possess stem cell properties for maintaining tissue homeostasis by sending signals to differentiated cells or supplying differentiated cells, and cells having properties of somatic cells that have already differentiated that receive various signals or commands from such cells, and is able to function through interaction between both of these types of cells. In the case of vertebrates, for example, interaction between mesenchymal cells and epithelial cells is essential for nearly all tissue and organ formation. In the case of hair follicles, mesenchymal cells in the form of hair papilla cells are responsible for stem cell-like properties, while epithelial cells in the form of keratinocytes are equivalent to cells having somatic cell-like properties in the sense that they differentiate into hair shafts (hair itself).

The difficulty encountered when forming organs by regenerative medicine lies in reaching a state of coexistence between cells having stem cell-like properties maintained in an undifferentiated state and cells that have already differentiated as in actual body tissue. In the prior art, even if epithelial cells and mesenchymal cells were able to be co-cultured, they either both ended up differentiating or both maintained an undifferentiated state, thereby preventing the reproduction of the coexistence of undifferentiated cells and differentiated cells so as to mimic actual body tissue.

DISCLOSURE OF THE INVENTION

An object of the present invention is to provide a cell mass capable of serving as a primitive organ-like structure by combining and culturing a plurality of types of differentiated somatic cells.

The present application includes the following inventions:
(1) a method of producing a cell mass capable of serving a primitive organ-like structure comprised of a plurality of somatic cell types of somatic origin, comprising:
  preparing cultures containing the plurality of types of somatic cells;
  mixing the plurality of types of somatic cell cultures followed by adding a Wnt signal activator to the mixed cell culture;
  subjecting the culture containing the Wnt signal activator to non-plate contact culturing over a predetermined time period; and
  replacing the medium of the culture cultured by the non-plate contact culturing with medium not containing Wnt signal activator and further culturing for a predetermined time period; wherein,
  at least one type of the plurality of somatic cells is maintained in an undifferentiated state;
(2) the method of (1), wherein the plurality of types of somatic cells is comprised of combinations of epithelial somatic cells and mesenchymal somatic cells, and the mesenchymal somatic cells are maintained in an undifferentiated state;
(3) the method of (2), wherein the epithelial somatic cells are keratinocytes, and the mesenchymal somatic cells are hair papilla cells;
(4) the method of (3), wherein hair follicles having a hair follicle inducing function are formed from the cell mass;
(5) the method of any of (1) to (4), wherein the Wnt signal activator is 6-bromoindirubin-3'-oxime (BIO);
(6) the method of any of (1) to (5), wherein the non-plate contact culturing method is the hanging drop method;
(7) a cell mass capable of serving as a primitive organ-like structure comprised of a plurality of somatic cell types of somatic origin, produced by a method comprising:
  preparing cultures containing the plurality of types of somatic cells;
  mixing the plurality of types of somatic cell cultures followed by adding a Wnt signal activator to the mixed cell culture;
  subjecting the culture containing the Wnt signal activator to non-plate contact culturing over a predetermined time period; and
  replacing the medium of the culture cultured by the non-plate contact culturing with medium not containing Wnt signal activator and further culturing for a predetermined time period; wherein, at least one type of the plurality of somatic cells is maintained in an undifferentiated state;

(8) the cell mass of (7), wherein the plurality of types of somatic cells is comprised of combinations of epithelial somatic cells and mesenchymal somatic cells, and the mesenchymal somatic cells are maintained in an undifferentiated state;

(9) the cell mass of (8), wherein the epithelial somatic cells are keratinocytes, and the mesenchymal somatic cells are hair papilla cells;

(10) the cell mass of (9), wherein hair follicles having a hair follicle inducing function are formed from the cell mass;

(11) the cell mass of any of (7) to (10), wherein the Wnt signal activator is 6-bromoindirubin-3'-oxime (BIO);

(12) the cell mass of any of (7) to (11), wherein the non-plate contact culturing method is the hanging drop method;

(13) a method for screening for drugs having a hair growth effect by applying a candidate drug to the cell mass of any of (9) to (12); and,

(14) the method of (13), which uses as an indicator an expressed amount of one or a plurality of genes selected from the group consisting of c-myc, BMP4 and IGFBP3 by the cell mass.

BRIEF DESCRIPTION OF THE DRAWINGS

FIG. 7 shows the expression of various genes in RNA originating in a cell mass of the present invention (1);

FIG. 8 shows the expression of Wnt3A gene in RNA originating in a cell mass of the present invention;

BEST MODE FOR CARRYING OUT THE INVENTION

Figure 1:
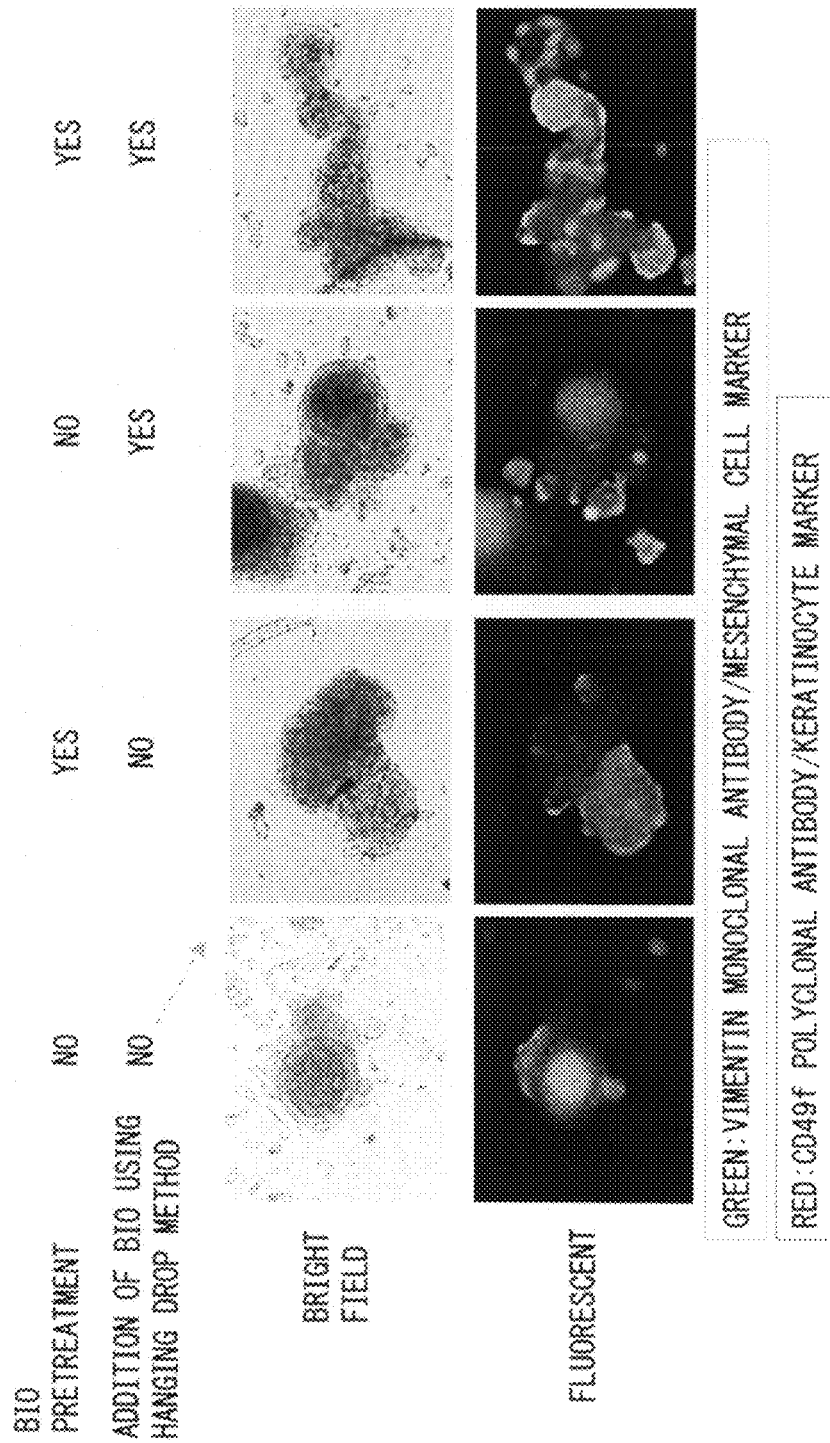
FIG. 1 is an immunostaining diagram (1) of a cell mass produced according to the method of the present invention showing staining of DP cells and NHEK cells.

According to the present invention, a cell mass can be provided that is capable as serving as a primitive organ-like structure comprised of a plurality of types of somatic cell types.

Somatic cells as referred to in the present invention refer to cells that have reached differentiation into cells that compose various organs of the body, and refer to cells that are the opposite of undifferentiated stem cells. The present invention is characterized by the use of two or more somatic cells, and preferably consists of various combinations thereof, such as a combination of an epithelial cell line and mesenchymal cells, a combination of endothelial cells and mesenchymal cells, or a combination of epithelial cells and mesenchymal cells.

There are no particular limitations on organs capable of being formed by the cell mass as claimed in the present invention, examples of which include various organs such as hair follicle, lung, kidney, liver, pancreas, spleen, heart, gallbladder, small intestine, colon, large intestine, joint, bone, tooth, blood vessel, lymph duct, cornea, cartilage, olfactory organ or auditory organ.

For example, in the case of desiring to form a hair follicle, keratinocytes of the head region are used for the epithelial cell line while hair papilla cells are used for the mesenchymal cells. The "epithelial cells" referred to here refer to cells that compose the majority of the epidermis or epithelium of skin, and arise from a single layer of basal cells in contact with the dermis. The epithelial cells may be epithelial cells originating in newborns (or fetuses), cells originating in mature skin such as the epidermis of dormant skin or the epidermis of growing skin, or a culture of cells having the morphology of keratinocytes. Such cells can be prepared from the skin of a desired donor animal according to methods known among persons with ordinary skill in the art. "Hair papilla cells" refer to cells located at the lowermost portion of hair follicles as mesenchymal cells that fulfill the role of a so-called control tower by sending activating signals to hair follicle epithelial stem cells for auto-regeneration of hair follicles. "Hair papilla cells" can be prepared by, for example, preparing a cell suspension by treating a dermal tissue fraction, obtained by removing epidermal tissue from skin tissue, with collagen, and then placing the cell suspension in frozen storage to destroy the hair follicle epithelial cells.

In addition, preparation can be carried out in the following manner for reconstruction of an olfactory organ, for example. First, a tissue site is excised at which is present a group of olfactory epithelial cells of a mammal such as a mouse. The tissue is then digested by treating with collagenase and separated by centrifugation to prepare a precipitated cell group. Then, the cell suspension is placed in a cell culture dish coated with collagen 1 or 4, and the suspension is rapidly aspirated in about 5 minutes to allow the highly adhesive olfactory epithelial cells to preferentially adhere. Epithelial cells remaining in the same dish can be transferred to a cell culture. Moreover, the majority of the remaining cells are epithelial cells. Although mesenchymal cells are present in the remaining aspirated suspension, by placing the suspension in a culture dish coated with fibronectin or gelatin and allowing to stand undisturbed for 4 hours or more in a suitable atmosphere such as that at 37° and 95% $CO_2$, the mesenchymal cells can be applied to cell culturing. The epithelial and mesenchymal cells prepared as described above can be used to reconstruct a new olfactory organ using a procedure similar to that used to reconstruct hair follicle organs.

Moreover, preparation can be carried out in the following manner for reconstruction of a renal glomerulus, for example. First, a site where tissue is present in the kidney of a mammal such as a mouse is excised. The tissue is digested by treating with collagenase and the separated by centrifugation followed by removing coarse matter with a 100 μm mesh filter. Then, glomerulus is collected in the mesh with a 40 μm mesh filter and a cell suspension is obtained by treating with trypsin. The cell suspension is placed in a cell culture dish coated with collagen 1 or 4 to preferentially adhere epithelial cells. As a result of this treatment, the majority of the cells are epithelial cells originating in the glomerulus.

On the other hand, in the case of kidney, mesenchymal cells present at the time of organogenesis are destroyed in the body. Thus, in the present invention, the following procedure can be employed to re-induce epithelial-mesenchymal interaction required for tissue reconstruction. The renal cells described above are used for the epithelial cells. Moreover, hair papilla cells or bone marrow mesenchymal cells of the same category are used as a substitute for the lost mesenchymal cells. Epithelial and mesenchymal cells as described above can be used to construct a new renal organ by using a technique similar to that used to reconstruct hair follicle organs.

Various mammals can be used without limitation as the origin of the cells as claimed in the present invention corresponding to the purpose thereof, examples of which include chimpanzees, other primates, domestic animals such as dogs or cats, farm animals such as cows, pigs, horses, sheep or goats, laboratory animals such as rabbits, rats, mice or guinea pigs, and more preferably nude mice, SCID mice or nude rats. In addition, although combinations thereof may be homogeneous combinations or heterogeneous combinations, homogeneous combinations are preferable.

There are no particular limitations on culture media effective for culturing the somatic cells as claimed in the present invention, and media commonly used for cell culturing can be used. For example, in the case of culturing mesenchymal cells, serum-containing media such as DMEM, MEM, F12 or Chang medium can be used preferably. In this case, serum concentration is 0 to 30% and preferably 10%, and basic fibroblast growth factor (bFGF), epidermal growth factor (EGF) and 2 mM L-glutamine are added as essential factors.

In the case of epithelial cells, serum-free medium optimized for keratinocytes, such as Epilife (registered trademark) and HuMedica (registered trademark) (both available from Kurabo) or Invitrogen SFM (available from Invitrogen), is preferable. Although keratinocytes can be prepared using the Green method depending on the case (Cell 1975 November; 6(13): 331-43, Serial cultivation of strain of human epidermal keratinocytes: the formation of keratinizing colonies from single cells, Rheinwalf J. G., Green H.), in this case, serum-containing medium used in the mesenchymal cell system described above can be used for the culturing thereof. Furthermore, examples of antibiotics that can be used for culturing both epithelial cells and mesenchymal cells include penicillin G, kanamycin, streptomycin and amphotericin B.

The present invention is characterized by the addition of a Wnt signal activator to a mixture of the plurality of somatic cells as described above followed by culturing thereof. Wnt signaling refers to a series of actions that demonstrate the function of transcription factors by promoting nuclear migration of β-catechin. These signals originate from cellular interaction that includes, for example, a series of processes in which a protein referred to as Wnt3A secreted from certain cells further acts on other cells causing nuclear migration of intracellular β catechin which acts as a transcription factor. This series of processes give rise to the initial phenomenon of organ construction in the example of epithelial-mesenchymal interaction. Wnt signaling is known to control cell proliferation and differentiation, organ formation and various cell functions such as cell migration during initial development. Although Wnt signaling is used when culturing ES cells for the purpose of inhibiting differentiation due to their function of maintaining an undifferentiated state (see, for example, Noboru Sato et al., Nature Medicine, Vol. 10, No. 1, January 2004), their utilization and effects during culturing of somatic cells are completely unknown.

There are no particular limitations on the Wnt signal activator, and any activator can be used provided it demonstrates inhibitory activity on glycogen synthase kinase-3 (GSK-3), examples of which include a bis-indolo (indirubin) compound, (BIO) ((2'Z,3'E)-6-bromoindirubin-3'-oxime), its acetoxime analog, BIO-acetoxime (2'Z,3'E)-6-bromoindirubin-3'-acetoxime), thiadiazolidine (TDZD) analog (4-benzyl-2-methyl-1,2,4-thiadiazolidine-3,5-dione) and oxothiadiazolidine-3-thione analog (2,4-dibenzyl-5-oxothiazolidine-3-thione), a thienyl α-chloromethyl ketone compound (2-chloro-1-(4,4-dibromo-thiophen-2-yl)-ethanone), a phenyl α-bromomethyl ketone compound (α-4-dibromoacetophenone), thiazol-containing urea compound (N-4-methoxybenzyl)-N'-(5-nitro-1,3-thiazol-2-yl)urea) and GSK-3β peptide inhibitors such as H-KEAPPAPPQSpP-NH$_2$.

There are no particular limitations on the amount of Wnt signal activator added, and the amount added is required to be an amount at which Wnt signal activation, or in other words, inhibition of GSK-3, is demonstrated and cell proliferation is not interrupted, is dependent on the type of cells to be grown, and is suitably determined by a person with ordinary skill in the art. For example, in the case of using BIO for the Wnt signal activator in hair papilla cells, although an amount added of, for example, about 0.1 to 10 μM is suitable, the amount added is naturally not limited thereto.

Another characteristic of the present invention is the subjecting of the mixture of the plurality of somatic cells, to which Wnt signal activator has been added, to non-plate contact culturing. Non-plate contact culturing refers to a method of culturing cells on an interface having a spherical surface so as not to allow adhesion of plate-adhering cells. An example of non-plate contact culturing is a hanging drop method (Keller, G. M. et al., Curr. Opin. Cell Biol., 7, 862-869 (1995)). The hanging drop method refers to adhering a drop (typically about 25 to 35 μL) of culture medium containing cultured cells onto the inside of the upper lid of a culture dish, carefully closing the lid so that the culture medium does not drop or run down, and culturing cells within the culture medium to be cultured in the form of an inverted drop due to surface tension. As a result of culturing in this manner, the effects on the cells attributable to contact with a flat surface as in the case of plate culturing can be minimized. Other examples of non-plate contact culturing methods include a formation method utilizing a semi-spherical cell culture dish that has been surface-treated in advance to prevent cell adhesion (for example, "Spheroid" commercially available from Sumitomo Bakelite) (referred to as the spheroid formation method), and a suspension method in which cells are aggregated in a suspended state by culturing in a nitrocellulose medium.

Although the temperature and duration of non-plate contact culturing varies dependent on the type of cells handled and the number of times they have been subcultured, culturing is carried out, for example, at 37° C. for 1 to 10 days and preferably for 3 to 7 days, and the medium is suitably replaced with the same medium as necessary.

Finally, the cells are further subjected to non-plate contact culturing in the absence of Wnt signaling by replacing the above medium with culture medium not containing Wnt signal activator. In this case as well, although the temperature and duration of culturing varies dependent on the type of cells handled and the number of times they have been subcultured, culturing is carried out, for example, at 37° C. for 1 to 10 days and preferably for 3 to 7 days, and the medium is suitably replaced with the same medium as necessary.

According to the present invention, a cell mass useful for, for example, hair follicle transplant, various organ transplants and partial transplants of microorgans comprising organs although not complete organs themselves, such as cornea, renal glomerulus, olfactory epithelial tissue or a cartilage site, can be efficiently and artificially produced. In addition, by using an artificially produced cell mass for drug evaluations, the action of a drug on organs of the body can be evaluated more accurately. In addition, transplant of the cell mass into immunosuppressed animals such as nude mice or SCID mice makes it possible to produce more complete organ-like tissue, and by ectopically producing human hair follicle or mouse kidney, for example, animal models can be prepared enabling evaluation of new drugs and evaluation of gene function. In particular, by inserting or altering a gene in cells when producing the cell mass, reconstructed organs having a reporter can be easily produced, thereby making it possible to accurately determine and investigate molecular behavior in the body at the tissue and organ levels.

In the cell mass according to the present invention, the epithelial cells are keratinocytes and the mesenchymal cells are hair papilla cells, and in the case of forming hair follicles having a hair follicle-inducing function, the cell mass can be used to evaluate drugs demonstrating a hair growth effect, and can be used, for example, by screening for such drugs. For example, in the case of applying a candidate drug of a hair growth drug to this cell mass and the growth of the cell mass is remarkable in comparison with a control, the drug can be assessed to have a hair growth effect, or can be assessed for the presence or absence of a hair growth effect by using increased expression of a gene that promotes hair growth, such as c-myc, as an indicator or by using inhibition of the expression of a gene that inhibits hair growth, such as BMP4 or IGFBP3, as an indicator.

EXAMPLES

Hair Papilla Cells

Human hair papilla cells were prepared from scalp tissue provided by a donor. After removing the dermal tissue, hair follicle sites present in fatty tissue were collected using forceps and ophthalmic scissors while viewing under a stereo microscope. The collected hair follicles were transferred to culture medium containing antibiotics, and sites of hair papilla cells were visually isolated and collected under the same microscope. The isolated hair papilla cells were cultured in the medium for one week or more at 37° C. and 95% $CO_2$ in a 10 cm round dish (TREP), after which they were submitted for experimental use. The medium used comprised Advanced DMEM (Invitrogen), 15% fetal bovine serum, 20 ng/ml of bFGF, 10 ng/ml of EGF, 2 mM L-glutamine, a mixture of penicillin, streptomycin and amphotericin (100-fold dilution), and 3.5 μl/50 ml of β-mercaptoethanol. The cells were suitably subcultured under the same conditions. During subculturing, the cells were separated with 0.5% trypsin/EDTA solutions transferred to a fresh dish and then sub-cultured in fresh medium of the same composition.

In the case of adding BIO (Calbiochem), the BIO was dissolved to 10 mM with dimethylsulfoxide (DMSO) and added to a concentration of 0.1 to 5 μM.

Keratinocytes

Keratinocytes from human normal neonatal foreskin were prepared in the manner described below. Foreskin tissue collected from a donor was treated overnight at 4° C. in PBS(−) in the presence of dispase enzyme. Only the epidermis was able to be collected in the form of a sheet as a result of this treatment, and this was digested with 0.25% trypsin enzyme using the same method as during subculturing, after which the tissue and medium were transferred to a collagen-treated culture dish and cultured. Humedia KG2 (Kurabo) was used for the medium. The cells were suitably subcultured under the same conditions. During subculturing, the cells were separated with 0.5% trypsin/EDTA solution, transferred to a fresh dish and then sub-cultured in fresh medium of the same composition. Cells collected and cultured in the manner described above were used in subsequent experimentation.

In the case of adding BIO (Calbiochem), the BIO was dissolved to 10 mM with dimethylsulfoxide (DMSO) and added to a concentration of 0.1 to 5 μM.

Hanging Drop Culturing

Medium Composition:

30% Advanced DMEM (Invitrogen), 2 mM L-glutamine, a mixture of penicillin and streptomycin (Invitrogen, 100-fold dilution) and 3.5 μl/50 ml of β-mercaptoethanol were mixed with Humedia KG-2 (Kurabo) at a ratio of 1:1.

In the case of adding BIO (Calbiochem), the BIO was dissolved to 10 mM with dimethylsulfoxide (DMSO) and added to a concentration of 0.1 to 5 μM.

Preparation Method:

Hair papilla cells were prepared to P3 or more (with P1 indicating one round of subculturing) in the presence or absence of BIO loading, while keratinocytes were prepared up to and including P3.

Each of the cells was diluted with each medium following trypsin treatment so as to obtain $1 \times 10^5$ cells.

In the case of adding BIO (Calbiochem), the BIO was dissolved to 10 mM with dimethylsulfoxide (DMSO) and added to a concentration of 0.1 to 5 μM.

25 to 35 μl of each culture medium was dispensed onto the inside of the upper lid of a square culture dish measuring 10 cm on a side and mixed to prepare dome-shaped droplets of a suitable size.

After carefully closing the lid, the cells were cultured at 37° C. in a 95% $CO_2$ atmosphere while ensuring that the culture medium did not drop down.

Three days later, the medium was replaced with the same medium as that used above.

After culturing for an additional four days, a portion of the medium was subjected to RT-PCR analysis (1) as described below. All of the remaining media was replaced with medium under conditions of the absence of BIO.

The media was replaced in the same manner on the third day, and cell masses that formed on day 7 were collected and subjected to immunostaining as described below.

Immunohistofluorescent Staining:

Each of the cell masses obtained with the hanging drop method were fixed for 5 minutes with 0.1% paraformaldehyde and submitted for staining. In addition, a portion of the cell masses were embedded in OCT solution without fixing and prepared into frozen sections with a cryostat followed by immunohistostaining.

Blocking was carried out for 6 hours with PBS(−) containing 13% bovine serum albumin (BSA).

Each of the primary antibodies indicated in the following table were diluted by 1/200 with the aforementioned PBS(−) containing 13% bovine serum albumin (BSA), added to each sample and allowed to react for 4 hours at 4° C.

The cells were washed three times with PBS(−) containing 0.02% Tween 20.

Fluorescent secondary antibody (see Excel file) diluted by 1/200 with the aforementioned PBS(−) containing 13% bovine serum albumin (BSA) was added to each sample. In addition, the nuclei of the cells were stained blue with DAPI (4'-6-diamidino-2-phenylindole).

The cells were observed with a fluorescent microscope (Olympus).

TABLE 1

| | Target Protein | Manufacturer | Description |
|---|---|---|---|
| Primary antibody | CD49f | Serotec | Rat anti-human/mouse CD49f |
| | Vimentin | YLEM | Monoclonal |
| | β-catechin | Becton Dickinson | Monoclonal |

| | Name | Manufacturer | Description |
|---|---|---|---|
| Secondary antibody | Goat anti-rat IgG TEXAX-RED conjugate | Jackson ImmunoResearch | Red |
| | Rabbit anti-mouse IgG ALEXAFLUOR 488 | Invitrogen | Yellow |

Here, since monoclonal antibody to vimentin specifically stains hair papilla cells and Cd49f polyclonal antibody specifically stains epidermal cells, application of vimentin and CD49f antibodies to immunocytostaining makes it possible to evaluate the attributes of cells present within the cell masses formed in this experimental system.

Figure 2:
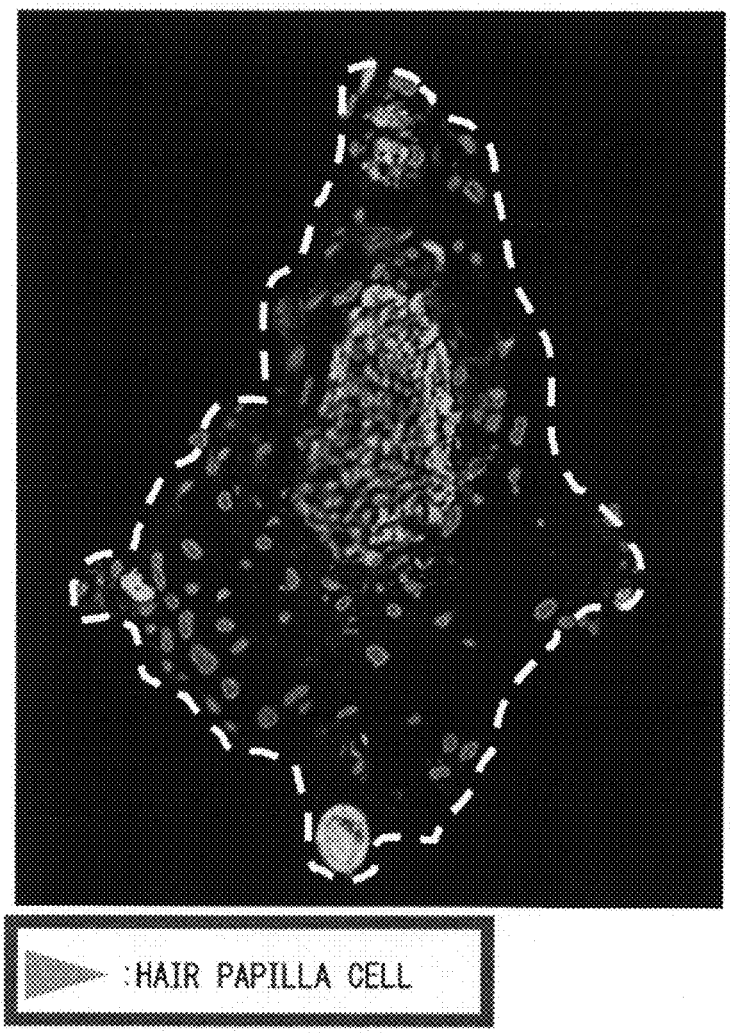
FIG. 2 is an immunostaining diagram (2) of a cell mass produced according to the method of the present invention showing localization of hair papilla cells in the cell mass.
Figure 3:
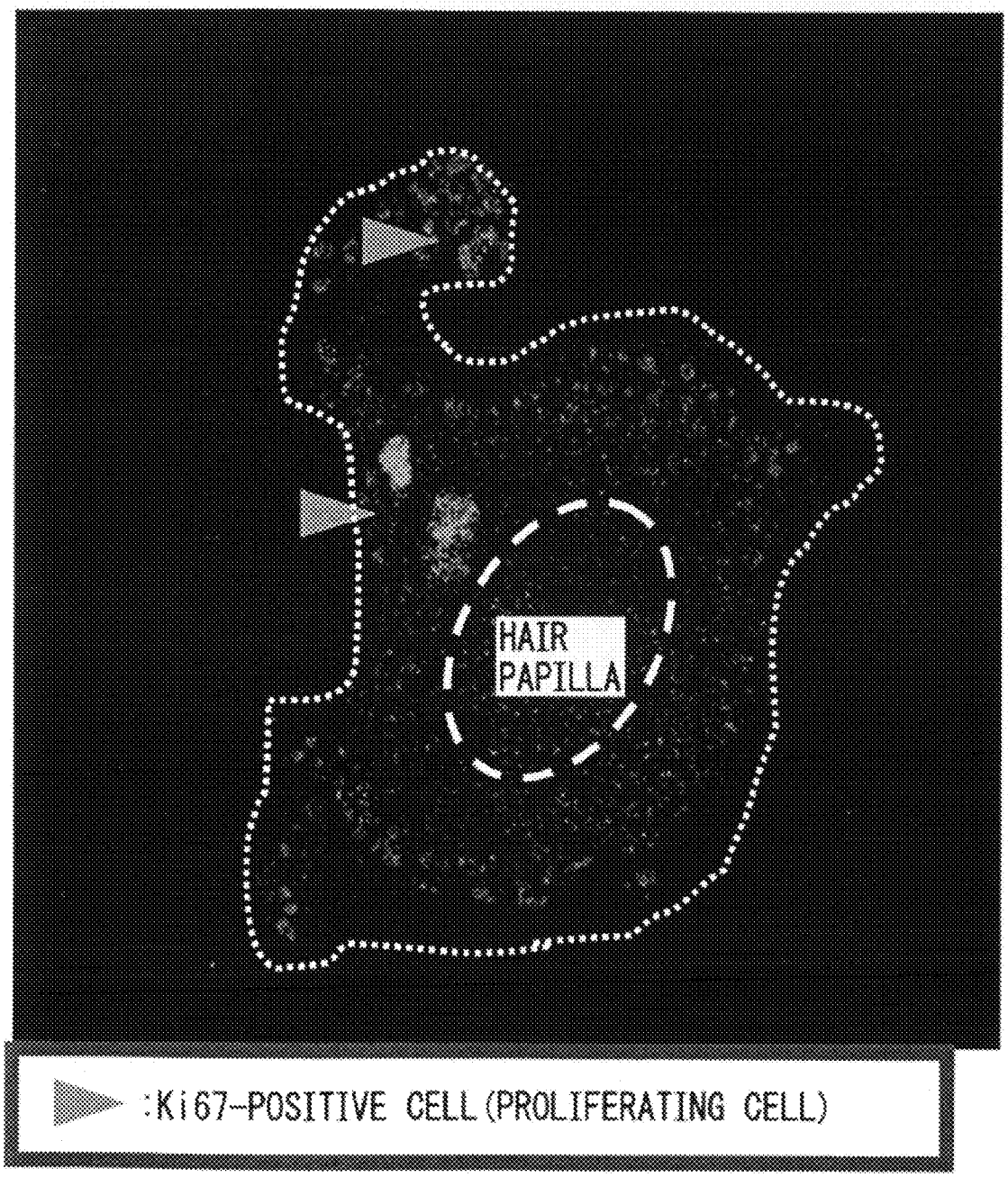
FIG. 3 is an immunostaining diagram (3) of a cell mass produced according to the method of the present invention showing cell proliferation in the cell mass.

FIG. 1 shows black-and-white photographs of the results of the microscopic observations described above. In the color version of this diagram, green coloring by vimentin antibody and red coloring by CD49f antibody can be distinguished, and each were able to be determined to be hair papilla cells and keratinocytes, respectively. In addition, as shown in FIG. 2, hair papilla cells were confirmed to be aggregated in the central portion of the cell mass. As a result of these diagrams, the cells were observed to be regularly arranged after having aggregated, and epithelial cells and mesenchymal cells were determined to be arranged in an orderly manner by this experimental system. After the cell masses formed following the addition of BIO, red-staining keratinocytes were determined to be growing in a regular manner in the form of branches within cell masses cultured in the absence of BIO. Moreover, as shown in FIG. 3, in the case of forming a cell mass by adding BIO, a central portion where hair papilla had aggregated and an end portion of the cell mass that extended in the form of a branch were found to be positive for the proliferation marker, KI67. On the basis of these results, although normal aggregated somatic cells usually enter a dormant state without growing, it was unexpectedly found that proliferation of cells occurred in the cell masses due to the addition of BIO.

In addition, β-catechin monoclonal antibody was used to mark stem cell-like properties. Since β-catechin is present in small amounts near the cell membrane of normal somatic cells, it can only be slightly detected by ordinary fluorescent immunostaining. However, in cells having stem cell-like properties, β-catechin acts as a transcription factor within the nucleus and is present in greater amounts. Moreover, since β-catechin accumulates in the nucleus, it can be confirmed to be strongly localized even by fluorescent immunostaining. In this experiment as well, since β-catechin was strongly stained at some specific sites of the cell mass and was confirmed to be accumulated at those sites, staining with β-catechin antibody can be said to be suitable for detection of cells having stem cell-like properties in the cell mass.

Figure 4:
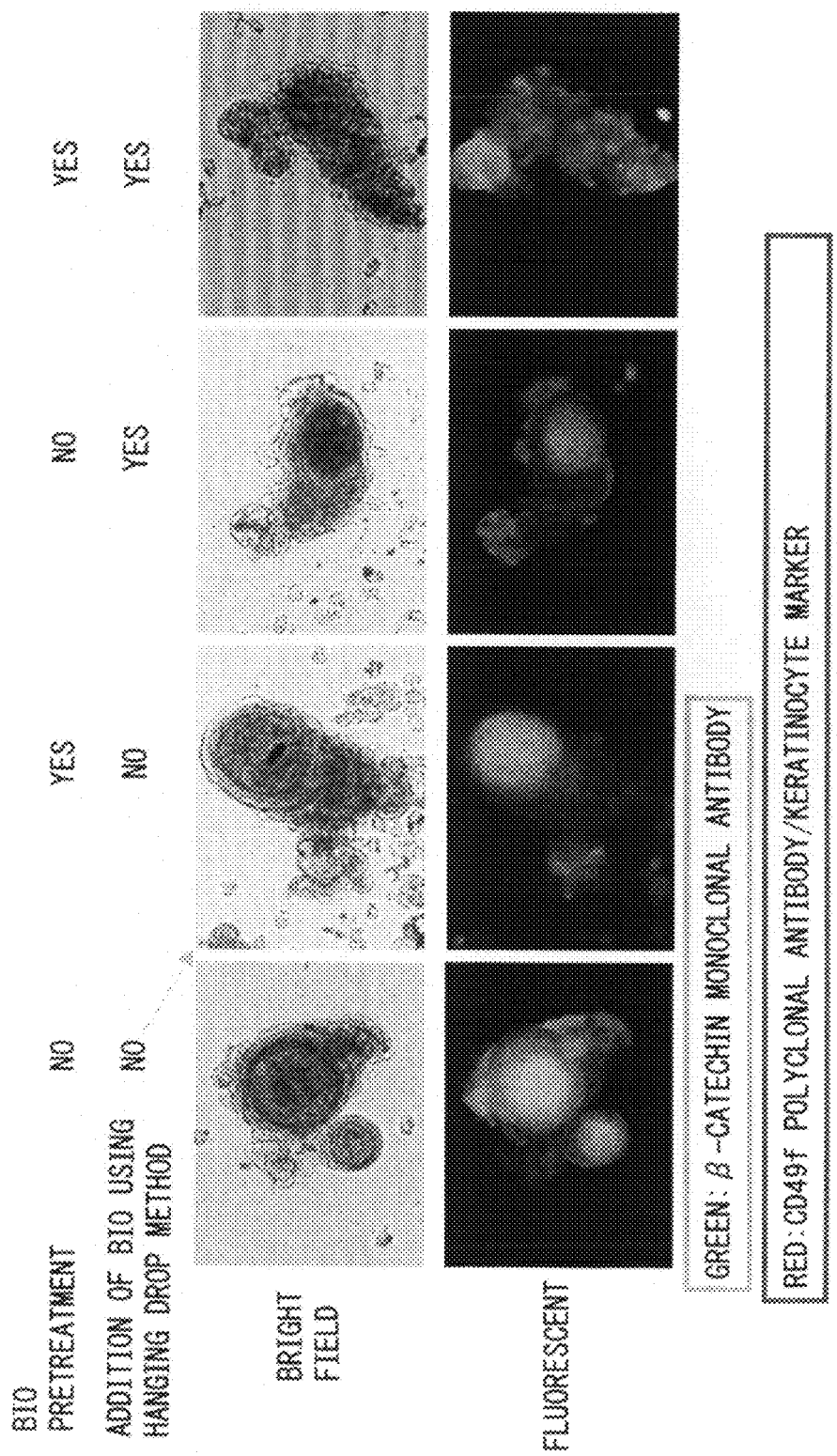
FIG. 4 is an immunostaining diagram (4) of a cell mass produced according to the method of the present invention showing staining of β-catechin and NHEK cells.

FIG. 4 is a black-and-white photograph showing the results of microscopic observation using the aforementioned β-catechin monoclonal antibody staining. In the color version of this diagram, sites stained with β-catechin antibody are shown in green, while keratinocytes are shown in red. β-catechin-positive cells were observed at sites emitting an intense green light, thus indicating the cells to have stem cell-like properties. What should be noted here is the presence of portions at which an intense yellow light is observed in the centers of spherical sites of the cell mass. These sites indicate β-catechin-positive keratinocytes. β-catechin-positive cells can be said to be cells having stem cell-like properties as previously described. On the other hand, there are no yellow sites at sites in keratinocytes extending from the cell mass in the form of branches. In other words, cells having stem cell-like properties and cells having normal somatic cell-like properties (keratinocytes) can be observed to both be present. This state is unable to be observed during ordinary culturing, and epithelial-mesenchymal interaction is reproduced as if it were present in vivo, thus indicating that undifferentiated and differentiated cell groups are growing by autonomously forming a cell mass.

Undifferentiated keratinocytes as referred to here indicate cells having a stem cell-like ability to constantly create keratinocytes that form hair in the manner of hair matrix cells. On the other hand, differentiated keratinocytes are limited as to the number of times they proliferate, and indicate so-called cells for which their cell fate is determined as they become hair. At the same time, although cells surrounding green spheres in the color version of FIG. 4 are thought to be hair papilla cells, the fact that hair papilla cells in the environment of this cell mass are β-catechin-positive cells is important in the same manner that Wnt signaling is important during follicle formation and at the start of growth in vivo.

Figure 5:
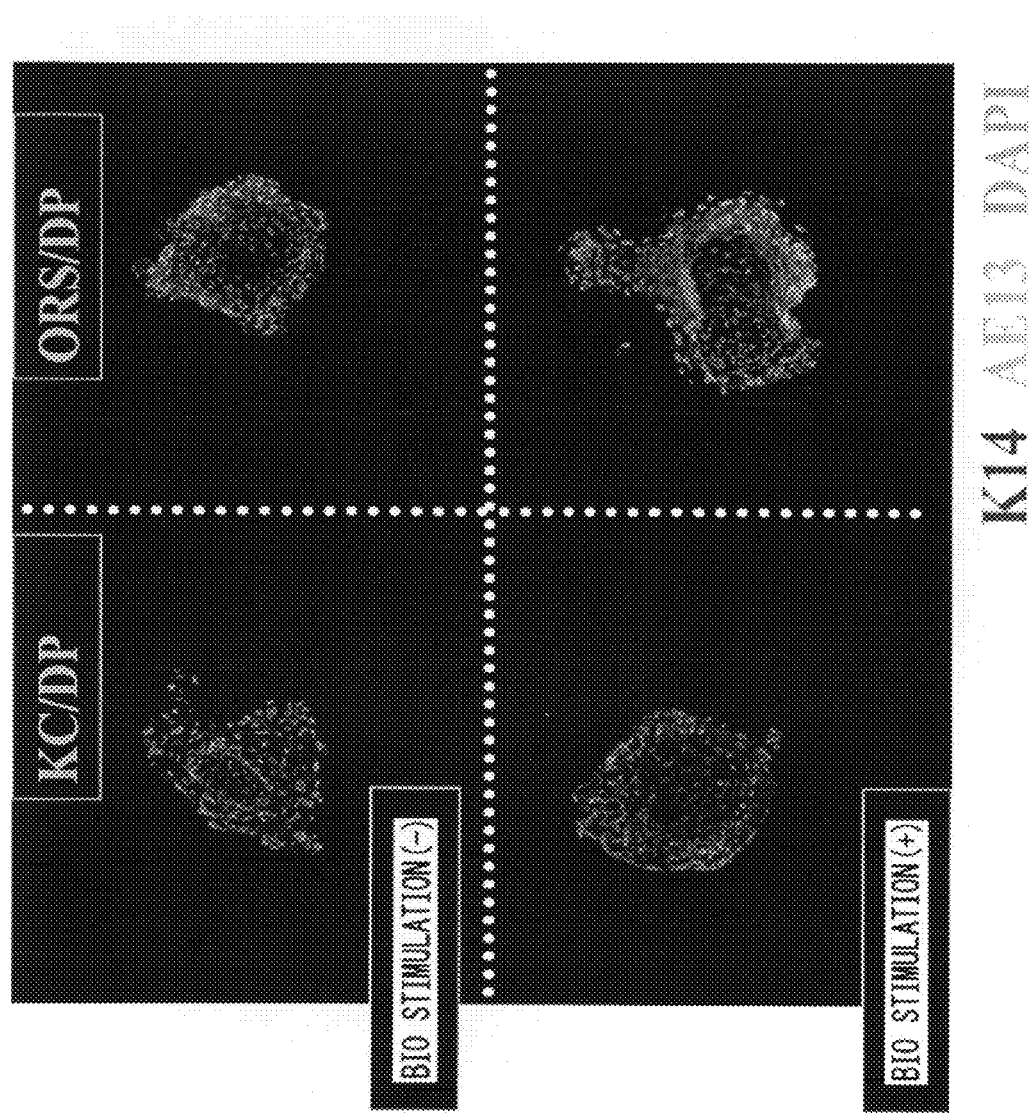
FIG. 5 is an immunostaining diagram (5) of a cell mass produced according to the method of the present invention showing expression of hair keratin in the cell mass.

Antibody to cytokeratin 14 (K14) expressed in epidermal keratinocytes and outer root sheath cells is used for the purpose of confirming that these cells have not differentiated to hair roots (red). Since AE13 monoclonal antibody, which specifically reacts to hair keratin (Lynch et al., J. Cell Biol., 103, 2593, 1986), recognizes 44K/46K acidic hair keratin dimer, it is used to mark differentiation into hair roots (green). Hair keratin is a hair follicle-specific structural protein that is essentially absent in normal epidermal keratinocytes. FIG. 5 is a black-and-white photograph showing the results of microscopic observation thereof. In the color version of this diagram, although sites stained by AE13 antibody are not observed in cell masses produced with hair papilla cells and epidermal keratinocytes, when stimulated with BID, staining is observed in some cell masses. In cell masses prepared with hair papilla cells and outer root sheath cells, sites stained by AE13 antibody can be confirmed in cases of the absence of BID stimulation, and staining by AE13 antibody is considerably enhanced by BID stimulation. On the other hand, since sites stained by both K14 antibody (red) and AE13 antibody (green) (yellow sites) are not observed in any of the cell masses, a change from undifferentiated cells expressing cytokeratin 14 to cells producing hair keratin is thought to have occurred.

Figure 6:
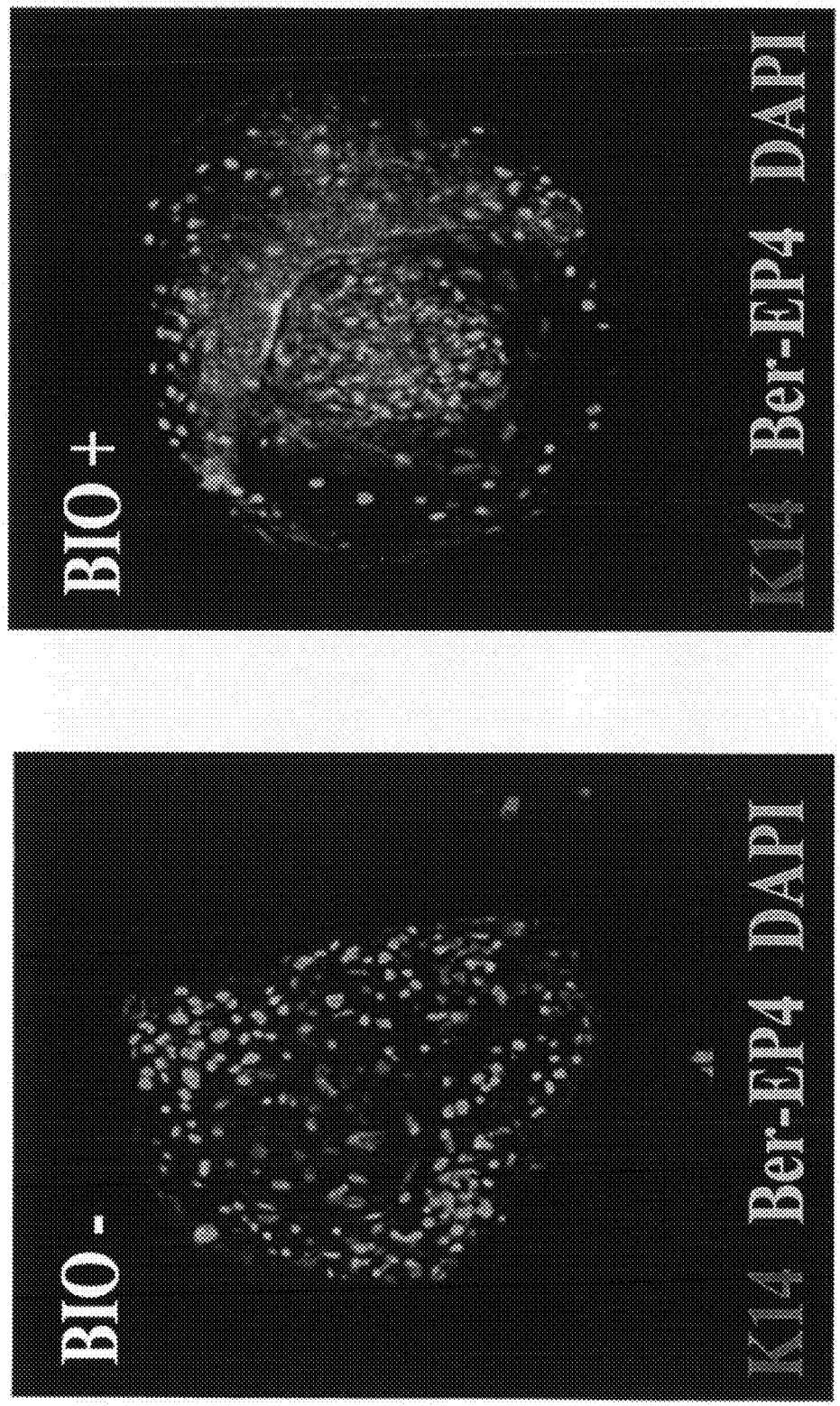
FIG. 6 is an immunostaining diagram (6) of a cell mass produced according to the method of the present invention showing expression of hair buds in the cell mass.

Ber-EP4 antibody to human epithelial antigen specifically expressed in hair buds during the hair growth stage (Ogawa, et al., Exp. Dermatol. 13, 401, 2004) is used to mark hair buds during hair growth (green). FIG. 6 is a black-and-white photograph showing the results of microscopic observation thereof. In the color version of this diagram, immunostaining (green) by Ber-EP4 antibody is clearly observed in the case of having stimulated cell masses prepared with hair papilla cells and outer root sheath cells with BIO. Since sites (yellow) stained by both K14 antibody (red) and Ber-EP4 antibody (green) are not observed, a change from undifferentiated cells expressing cytokeratin 14 to cells differentiated to hair buds expressing Ber-EP4 is thought to have occurred.

RT-PCR Analysis (1)

RNA was extracted from each sample using Trizol (Invitrogen). An equivalent of 200 ng of each RNA was reverse transcribed to cDNA with a reaction system consisting of 50

μl of RevTraACE (Toyobo). 1 μl of the resulting samples was applied to a PCR reaction in a 50 μl system using the primers listed below. KOD-DASH (Toyobo) was used for the enzyme, and the reaction protocol consisted of 60 seconds at 95° C., 40 cycles of 30 seconds at 95° C., 15 seconds at 63° C. and 30 seconds at 72° C., followed by 60 seconds at 72° C.

10 μl of the reaction solution was electrophoresed at 100 V in 2% agarose gel (Cosmobio)/TAE buffer. A 100 bp ladder marker (Toyobo) was used for the DNA size marker.

The primers used are listed in the following table, and the PCR results are shown in FIG. 7.

TABLE 2

|  | Sense primer (forward chain) | Anti-sense primer (reverse chain) |
|---|---|---|
| Lef-1 | gctatcaaccagattcttggcagaagg (SEQ ID NO. 1) | cagctgtcattcttggacctgtacctg (SEQ ID NO. 2) |
| SHH | ctacgagtccaaggcacatatccactg (SEQ ID NO. 3) | tccaggaaagtgaggaagtcgctgtag (SEQ ID NO. 4) |
| STAT-3 | aagaccggcgtccagttcactactaaag (SEQ ID NO. 5) | ggtcaagtgtttgaattctgcagagagg (SEQ ID NO. 6) |
| Versican | tccaagttatgttggtgcactttgtgag (SEQ ID NO. 7) | tcaaacatcttgtcattgaggcctatcc (SEQ ID NO. 8) |
| TWIST-1 | ggccaggtacatcgacttcctctac (SEQ ID NO. 9) | tctccttctctggaaacaatgacatc (SEQ ID NO. 10) |
| β-actin | cgcgagaagatgacccagatcatg (SEQ ID NO. 11) | ccacaggactccatgcccacg (SEQ ID NO. 12) |

β-actin was used as a control for the entire experiment.

Lef-1 is a downstream gene of Wnt signaling, and as shown in FIG. 7, was detected in this experimental system both in the presence and absence of BIO. The observation of expression of Lef-1 gene means that Wnt signals are acting on the cells. Thus, Wnt signaling can be understood to be functioning by addition of BIO in this experimental system.

SHH (Sonic Hedge Hog) is a gene that is involved during tissue formation, and as shown in FIG. 7, was not detected in this experimental system either in the presence or absence of BIO. SHH is a gene that is transcribed and expressed in response to Wnt and Lef-1 signals. Expression of this gene indicates that Wnt signaling is acting on the cells and that linked gene expression such as that which occurs in vivo is occurring. At the same time, SHH is a protein responsible for epithelial-mesenchymal intercellular signaling, and simultaneously suggests the occurrence of epithelial-mesenchymal interaction.

STAT-3 (Signal Transducer and Activator of Transcription 3) is a gene related to induction of hair follicles, and as shown in FIG. 7, was detected prominently in the presence of BIO as compared with in the absence thereof. STAT-3 is a so-called intracellular signal transduction protein involved in self-proliferation of stem cells. Acceleration of this gene is an essential factor for self-proliferation and maintaining universality in embryonic stem cells, and is one of the markers used to indicate stem cell-like properties thereof. At the same time, as is described in the paper by Sano, S. et al. (Nature Med. 11: 43-49, 2005, "Stat3 links activated keratinocytes and immunocytes required for development of psoriasis in a novel transgenic mouse model"), since this is also an extremely important gene for transition to the hair growth stage, it is suggested that acceleration of transcription of STAT-3 in this experimental system is a normal stage during subsequent growth into hair follicles. At the same time, the STAT-3 signal itself is not directly affected by BIO (Sato, N. et al., Nat. Med. 2004, January; 10(1):55-63, Epub 2003 Dec. 21, "Maintenance of pluripotency in human and mouse embryonic stem cells through activation of Wnt signaling by a pharmacological GSK-3 specific inhibitor"). In other words, acceleration of STAT-3 during addition of BIO indicates that a stem cell maintenance system is created within cells by epithelial-mesenchymal interaction.

TWIST-1 is marker for embryonic mesenchymal stem cells, and suggests that hair papilla cells have extremely high stem cell-like properties. Since expression of TWIST-1 in somatic cells is limited to an extremely rare type of cells containing bone marrow mesenchymal stem cells, hair papilla cells can be said to be cells having a high degree of stem cell-like properties despite being somatic cells. In the RT-PCR experiment of FIG. 7, RT-PCR is carried out using equal amounts of whole RNA for the templates. The reason for expression appearing to decrease in the presence of BIO is due to a relative decrease in the number of hair papilla cells among the total number of cells as can be observed from FIG. 1 and FIG. 2. In conclusion, even when considering variations in expressed amounts, the continued presence of cells expressing TWIST-1 gene suggests that hair papilla cells capable of having stem cell-like abilities are continuing to be present in this experimental system.

Versican gene is a hair growth marker known to be strongly expressed in hair papilla cells during induction of hair growth (Kishimoto, et al., Proc. Natl. Acad. Sci. USA (1999), pp. 7336-7341). In the RT-PCR experiment of FIG. 7, the reason for expression appearing to decrease in the presence of BIO is due to a relative decrease in the number of hair papilla cells among the total number of cells as can be observed in FIG. 1 and FIG. 2. In conclusion, even when considering variations in expressed amounts, the continued presence of cells expressing Versican gene suggests that hair papilla cells capable of inducing hair growth are continuing to be present in this experimental system.

Based on the changes in the expression levels of each gene, undifferentiation of epithelial and mesenchymal cells is maintained due to the direct effects of BIO within the cell mass, and an action mimicking the epithelial-mesenchymal action induced by Wnt signaling can be said to have occurred. In addition, since the appearance of stem cell-like properties unrelated to Wnt signaling are observed as with STAT-3, the effect of BIO contributes to the creation of a cell mass having autonomic cell interaction and the ability to proliferate.

Wnt3A RT-PCR

Hair papilla cells were prepared to 23 (with P1 indicating one round of subculturing) in the presence of BIO loading, while keratinocytes were prepared up to and including P3.

Each of the cells was diluted with each medium following trypsin treatment so as to obtain $3\times10^3$ cells.

BIO (Calbiochem) was dissolved to 10 mM with dimethylsulfoxide (DMSO) and added to a concentration of 0.1 to 5 μM.

25 to 35 μl of each culture medium was dispensed onto the inside of the upper lid of a square culture dish measuring 10 cm on a side and mixed to prepare dome-shaped droplets of a suitable size.

After carefully closing the lid, the cells were cultured at 37° C. in a 95% $CO_2$ atmosphere while ensuring that the culture medium did not drop down.

Three days later, the medium was replaced with the same medium as that used above. The samples were collected on the 7th day and submitted for RT-PCR analysis (2) as described below ("0 day" in FIG. 8). The medium used for the same remaining cells was replaced with medium under conditions of the absence of BIO to induce differentiation, after which the samples collected on the 3rd day were submitted for RT-PCR analysis (2) as described below ("3 days" in FIG. 8).

RT-PCR Analysis (2)

RNA was extracted from the samples using Trizol (Invitrogen). An equivalent of 200 ng of each RNA was reverse transcribed to cDNA with a reaction system consisting of 50 μl of RevTraACE (Toyobo). 1 μl of the resulting samples was applied to a PCR reaction in a 50 μl system using the primers listed below. KOD-DASH (Toyobo) was used for the enzyme, and the reaction protocol consisted of 2 minutes at 94° C., 32 cycles of 30 seconds at 94° C., 10 seconds at 63° C. and 30 seconds at 72° C., followed by 2 minutes at 72° C.

```
Sense primer (forward chain):
                                    (SEQ ID NO. 13)
caggaactacgtggagatcatg Anti-sense primer (reverse chain):
                                    (SEQ ID NO. 14)
ccatcccaccaaaactcgatgtc
```

10 μl of the reaction solution was electrophoresed at 100 V in 2% agarose gel (Cosmobio)/TAE buffer. Target bands were detected after visualizing with ethidium bromide.

The results are shown in FIG. 8. The arrow in the drawing indicates a Wnt3A band. The expression itself of Wnt3A is rare, is mainly expressed by epithelial cells, and is known to be a gene involved in organogenesis and epithelial cell-mesenchymal cell interaction. As shown in the drawing, in contrast to expression of Wnt3A not being observed at all in cells in which Wnt signaling was activated by culturing in the presence of BIO, expression of Wnt3A was observed in cells in which cell differentiation was subsequently induced by removal of BIO. Accordingly, in this experimental system, keratinocyte differentiation, and what is more, autonomous organogenesis were clearly determined to be induced by culturing in the presence of BIO followed by culturing after removing BIO.

Wnt10B RT-PCR

Hair papilla cells were prepared to P3 (with P1 indicating one round of subculturing) in the absence of BIO loading, while outer root sheath cells were prepared up to and including P3.

Each of the cells was diluted with each medium following trypsin treatment so as to obtain $3\times10^3$ cells.

BIO (Calbiochem) was dissolved to 10 mM with dimethylsulfoxide (DMSO) and added to a concentration of 0.1 to 5 μM.

25 to 35 μl of each culture medium was dispensed onto the inside of the upper lid of a square culture dish measuring 10 cm on a side and mixed to prepare dome-shaped droplets of a suitable size.

After carefully closing the lid, the cells were cultured at 37° C. in a 95% $CO_2$ atmosphere while ensuring that the culture medium did not drop down.

Three days later, the medium was replaced with the same medium as that used above. The samples were collected on the 7th day and submitted for RT-PCR analysis (3) as described below ("day 7" in FIG. 9). The medium used for the same remaining cells was replaced with medium without BIO to induce differentiation, after which samples collected after 10 and 14 days were submitted for RT-PCR analysis (3) as described below ("day 10" and "day 14" in FIG. 9).

RT-PCR Analysis (3)

RNA was extracted from the samples using Trizol (Invitrogen). An equivalent of 200 ng of each RNA was reverse transcribed to cDNA with a reaction system consisting of 50 μl of RevTraACE (Toyobo). 4 μl of the resulting samples were applied to a quantitative PCR system (LightCycler System, Roche) in a 20 μl system using the primers listed below. The reaction protocol of LightCycler FastStart DNA Master SYBR Green (Roche) (consisting of 40 cycles of 10 seconds at 95° C., 10 seconds at 63° C. and 15 seconds at 72° C.) was used.

```
Sense primer (forward chain):
                                    (SEQ ID NO. 15)
gaagttctctcgggatttcttggatcc Anti-sense primer (reverse chain):
                                    (SEQ ID NO. 16)
cggttgtgggtatcaatgaagatgg
```

Figure 9:
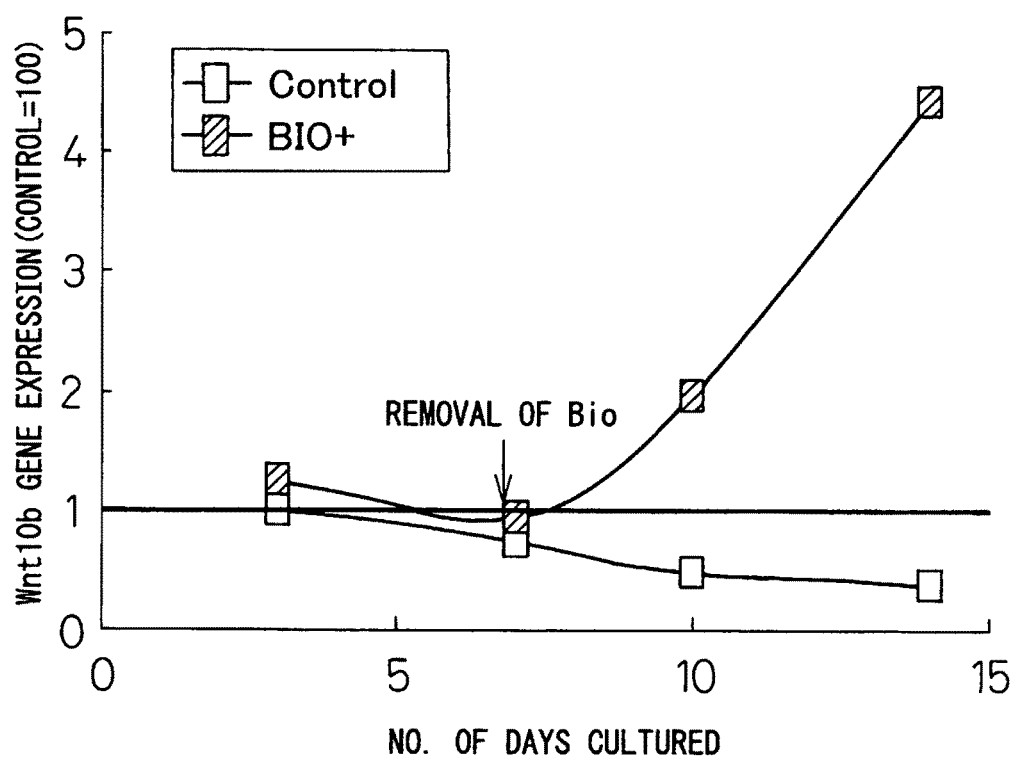
FIG. 9 shows the expression of Wnt10B gene in RNA originating in a cell mass of the present invention.

The results are shown in FIG. 9. All data was expressed as the relative expressed amount based on the expressed amount after 3 days in the case of not loading the cell mass with BIO. Wnt10B is mainly expressed by epithelial cells during the stages of hair follicle morphogenesis and hair growth, and is known to be a gene involved in an epithelial cell-mesenchymal cell interaction. As shown in the drawing, in contrast to expression of Wnt10B only being observed to be expressed to about the same level as that of a control cultured in the absence of BIO in cells in which Wnt signaling was activated by culturing in the presence of BIO as long as the cells were cultured in the presence of BIO, expression of Wnt10B increased over time in cells in which cell differentiation was subsequently induced by removing BIO. Accordingly, in this experimental system, differentiation of follicular epithelial cells (outer root sheath cells), and what is more, autonomous organogenesis were clearly determined to be induced by culturing in the presence of BIO followed by culturing after removing BIO.

Reactivity of Cell Mass to Hair Growth Stimulator, Cyclosporine A

Hypertrichosis is known to be a side effect of the immunosuppressant, cyclosporine A (Lutz, et al., Skin Pharmacol. 7, 101, 1994), and cyclosporine A has been clearly determined to demonstrate hair growth action (Paus, et al., Lab. Invest. 60, 365, 1989) and hair growth promoting action (Taylor, et al., J. Invest. Dermatol., 100, 237, 1993).

Hair papilla cells were prepared to P3 (with P1 indicating one round of subculturing) in the absence of BIO loading, while outer root sheath cells were prepared up to and including P3.

Each of the cells was diluted with each medium following trypsin treatment so as to obtain $3 \times 10^3$ cells.

25 to 35 μl of each culture medium was dispensed onto the inside of the upper lid of a square culture dish measuring 10 cm on a side and mixed to prepare dome-shaped droplets of a suitable size.

After carefully closing the lid, the cells were cultured at 37° C. in a 95% $CO_2$ atmosphere while ensuring that the culture medium did not drop down.

Three days later, the medium was replaced with the same medium as that used above containing cyclosporine A. Cyclosporine A was dissolved to 10 mM with ethanol and added to a concentration of 0.1 to 10 μM.

The samples were collected three days after addition of cyclosporine A and submitted for RT-PCR analysis (4) as described below.

RT-PCR Analysis (4)

RNA was extracted from the samples using the RNeasy Kit (Qiagen). An equivalent of 200 ng of each RNA was reverse transcribed to cDNA with a reaction system consisting of 20 μl of SuperScript II (Invitrogen). 1 μl of the resulting samples were applied to a quantitative PCR system (LightCycler System, Roche) in a 20 μl system using the primers listed below. The reaction protocol of LightCycler FastStart DNA Master SYBR Green (Roche) (consisting of 40 cycles of 10 seconds at 95° C., 10 seconds at 58° C. and 15 seconds at 72° C.) was used.

```
BMP4:
Sense primer (forward chain):
                                          (SEQ ID NO. 17)
gggcacctcatcacacgact Anti-sense primer (reverse chain):
                                          (SEQ ID NO. 18)
ggcccaattcccactccctt c-myc:
Sense primer (forward chain):
                                          (SEQ ID NO. 19)
ttctctccgtcctcggaattctctg Anti-sense primer (reverse chain):
                                          (SEQ ID NO. 20)
cagcagaaggtgatccagactctgac IGFBF3:
Sense primer (forward chain):
                                          (SEQ ID NO. 21)
acagccagcgctacaaagtt Anti-sense primer (reverse chain):
                                          (SEQ ID NO. 22)
tagcagtgcacgtcctcctt
```

Figure 10:
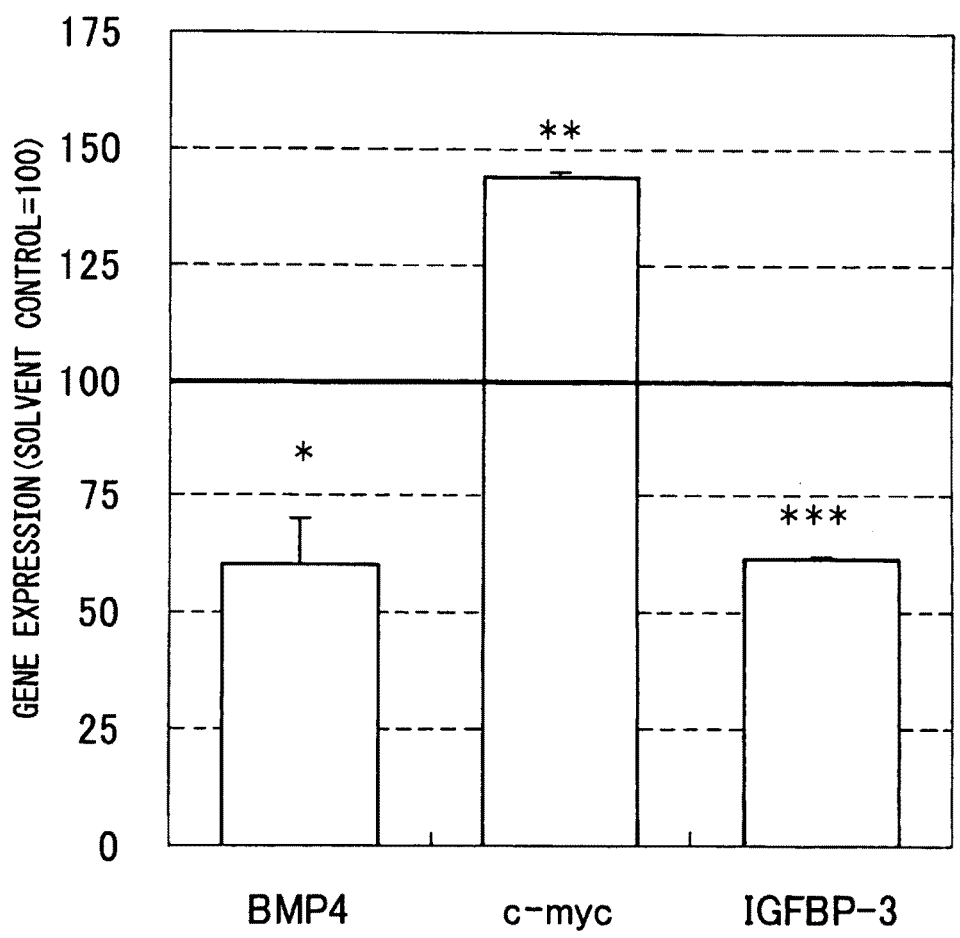
FIG. 10 shows the expression of various genes in RNA originating in a cell mass of the present invention (2).

The results are shown in FIG. 10. All data was expressed as the relative expressed amount based on the case of not adding Cyclosporine A. BMP4 is known to be a gene that is mainly expressed by hair papilla cells during the hair follicle morphogenesis and hair growth stages and acts to inhibit epithelial cell-mesenchymal cell interaction (Hens, et al., Development 134, 1221, 2007). As shown in the drawing, the expressed amount of BMP4 decreased significantly to about 60%. In addition, c-myc is known to be a gene that is strongly expressed in the bulge region during the hair development stage and in hair matrix cells during the growth stage, and acts positively on the proliferation of follicular epithelial cells (Bull, J. J. et al., Invest. Dermatol. 116, 617, 2001). As shown in the drawing, expression of c-myc increased to nearly 1.5 times that of the control. Moreover, IGFBP3 is known to be factor that inhibits hair growth (Weger, et al., J. Invest. Dermatol. 125, 847, 2005), and the expression thereof has been clearly demonstrated to increase during the dormant stage (Schlake, et al., Gene Expr. Patterns 4, 141, 2004). As shown in the drawing, expression of IGFBP3 significantly decreased to about 60%. Accordingly, genes involved in hair development and hair growth used in this experimental system were determined to be altered by Cyclosporine A, thereby demonstrating that this experimental system can be used to evaluate the effects of drugs on hair development and hair growth.

The invention claimed is:

1. A method of producing a cell mass capable of serving as a primitive organ-like structure comprised of combinations of keratinocytes and hair papilla cells, comprising:
   preparing cultures containing keratinocytes and hair papilla cells;
   mixing said keratinocytes and hair papilla cell cultures followed by adding a Wnt signal activator demonstrating an inhibitory activity on glycogen synthase-kinase-3 (GSK-3) to the mixed cell culture;
   subjecting the culture containing the Wnt signal activator to hanging drop method or spheroid formation method over a predetermined time period; and
   replacing the medium of the culture cultured by the hanging drop method or spheroid formation method with medium not containing Wnt signal activator and further culturing for a predetermined time period; wherein, at least one type of the keratinocytes and the hair papilla cells is maintained in an undifferentiated state.

2. The method according to claim 1, wherein hair follicles having a hair follicle inducing function are formed from the cell mass.

3. The method according to claim 1, wherein the Wnt signal activator is 6-bromoindirubin-3'-oxime (BIO).

4. The method according to claim 1, wherein the Wnt signal activator demonstrating an inhibitory activity on GSK-3 is selected from bis-indolo(indirubin) compound, (2'Z,3'E)-6-bromoindirubin-3'-oxime, (2'Z,3'E)-6-bromoindirubin-3'-acetoxime, 4-benzyl-2-ethyl-1,2,4-thiadiazolidine-3,5-dione, 2,4-dibenzyl-5-oxothiazolidine-3-thione, 2-chloro-1-(4,4-dibromo-thiophen-2-yl)-ethanone, α-4-dibromoacetophenone, N-(4-methoxybenzyl)-N'-(5-nitro-1,3-thiazol-2-yl)urea) and a GSK-3β peptide inhibitor.

* * * * *

UNITED STATES PATENT AND TRADEMARK OFFICE
CERTIFICATE OF CORRECTION

PATENT NO. : 8,563,309 B2
APPLICATION NO. : 12/306649
DATED : October 22, 2013
INVENTOR(S) : Fujiwara et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 889 days.

Signed and Sealed this

Fifteenth Day of September, 2015

Michelle K. Lee
*Director of the United States Patent and Trademark Office*